(12) United States Patent
Pastorino (10) Patent No.: US 9,510,079 B1
(45) Date of Patent: Nov. 29, 2016

(54) DUAL FUNCTION SOUND ATTENUATING AND ENHANCING HEADPIECE

(71) Applicant: Gustav Y Pastorino, Fremont, CA (US)

(72) Inventor: Gustav Y Pastorino, Fremont, CA (US)

( * ) Notice: Subject to any disclaimer, the term of this patent is extended or adjusted under 35 U.S.C. 154(b) by 0 days.

(21) Appl. No.: 14/952,730

(22) Filed: Nov. 25, 2015

(51) Int. Cl.
*H04R 25/00* (2006.01)
*H04R 1/10* (2006.01)
*H04R 5/033* (2006.01)
*A61F 11/00* (2006.01)

(52) U.S. Cl.
CPC .......... *H04R 1/1041* (2013.01); *A61F 11/008* (2013.01); *H04R 1/105* (2013.01); *H04R 1/1008* (2013.01); *H04R 1/1058* (2013.01); *H04R 1/1066* (2013.01); *H04R 1/1091* (2013.01); *H04R 5/0335* (2013.01); *H04R 2201/105* (2013.01)

(58) Field of Classification Search
CPC .. H04R 1/1008; H04R 1/1041; H04R 1/105; H04R 1/1058; H04R 1/1066; H04R 1/345; H04R 5/033; H04R 5/0335; H04R 2201/105; A61F 11/008; A61F 11/14
USPC ...... 381/309, 71.6, 370, 371, 372, 373, 374, 381/376, 381; 181/129, 136; 379/430; 128/866, 867; 2/209
See application file for complete search history.

(56) References Cited

U.S. PATENT DOCUMENTS

| | | | | |
|---|---|---|---|---|
| 2,537,201 A | * | 1/1951 | Amfitheatrof | A61F 11/008 181/136 |
| 3,661,225 A | * | 5/1972 | Anderson | A61F 11/14 128/866 |
| 4,041,256 A | * | 8/1977 | Ohta | H04R 1/1058 381/371 |
| 5,345,512 A | * | 9/1994 | Lee | H04R 1/1066 181/136 |

* cited by examiner

*Primary Examiner* — Huyen D Le (57) ABSTRACT

A dual function sound attenuating and enhancing headpiece is a device for blocking sound that the user does not wish to hear. The device additionally allows the user to enhance or otherwise alter sound. A first acoustic assembly and a second acoustic assembly are worn on the user's ears and include at least one acoustic-enhancing and attenuating cover that may be closed to block sound entirely. The at least one acoustic-enhancing and attenuating cover may be opened to a desired degree in order to produce an acoustic effect on incoming sound. The at least one acoustic-enhancing and attenuating cover is opened and closed via an at least one servomotor. A wireless control unit and a wireless communications module allow the user to open or close the at least one acoustic-enhancing and attenuating cover via a mobile device. At least one power supply provides electrical power to the device.

19 Claims, 12 Drawing Sheets

DETAIL A

DETAIL B

DUAL FUNCTION SOUND ATTENUATING AND ENHANCING HEADPIECE

FIELD OF THE INVENTION

The present invention relates generally to a device for altering the user's audio experience. More specifically, the present invention is a dual function sound attenuating and enhancing headpiece that provides the user with a degree of selective hearing, while also being advantageous for hearing protection in noisy environments.

BACKGROUND OF THE INVENTION

Noise-induced hearing loss (NIHL) often results from overstimulation of the hearing cells causing death of the hearing cells. The hearing loss can be caused by a single intense noise, or alternatively, gradually over time due to consistent exposure to noise. Both acoustic NIHL and gradually developing NIHL can be prevented through the use of hearing protection such as earplugs and earmuffs.

The present invention is a dual function sound attenuating and enhancing headpiece. The present invention allows the user to nearly block all noise from reaching his or her ears, similar to a pair of earplugs or earmuffs. However, in the event that the user wishes to focus his or her hearing on a specific area, the present invention physically allows the user to hear sound, physically amplified to preference, from the specific area while minimizing sound from all other areas. The selective hearing capability provided by the present invention grants the user a degree of freedom over his or her listening experience. The present invention is additionally able to produce an acoustic effect on sound to enhance the listening experience for the user.

The physical manipulation of sound can produce effects that are complex or difficult to replicate. An example of this can be found when juxtaposing the acoustic resonance qualities of a classical violin relative to today's electric violins. The acoustic qualities of an electric violin are clearly distinct due to the digital acoustic manipulation of the created sound emanating from a speaker when compared to the sound resonating directly from a classical violin, which relies on the shape of the sound box and vibrations of certain parts (e.g. the sound post). The listener may prefer the non-digital acoustics over the digital. In this sense, an earpiece or earmuff that is able to physically alter sound rather than digitizing the sound at the ear is advantageous to purely digital acoustic regulation.

In contrast to the failures and difficulties experienced by electric violins in attempting to recreate the resonant effects of sound projected from classical violins, the present invention serves as a physical instrument to alter sound at the user's discretion. The present invention manipulates sound directly at the point of reception, directly at the ear. In this capacity, the user is able to adjust the present invention in order to attenuate undesired ambient noise, reducing the decibel level from 120 dB and above, to a manageable level between 15 dB and 60 dB. Depending on the material of the design, the decibel level can near 0 dB. Alternatively, the user may adjust the present invention in order to produce a desired physical acoustic effect by slowing the sound waves near the ear, through its shape as a resonating chamber, on the sound as the sound is received at the ear. Similar to a musical instrument, through opening and closing at different rates, the present invention is able to drown out sound at different rates, allowing the present invention to create a fading effect or to rhythmically mute sound. The effects are physical in nature and autonomously controlled by the user, much like how a musician plays an instrument, and the listener acts upon the music or sound to change the dynamics (volume) of the sound. The harmonization with ambient sounds and music produces a desired alteration of sound at moments that are preferred by the user. The present invention is controlled electronically and wirelessly, allowing other users or an application to control for attenuating or enhancing the incoming acoustic effects to a user or users while one or more units of the present invention are operating.

DETAIL DESCRIPTIONS OF THE INVENTION

All illustrations of the drawings are for the purpose of describing selected versions of the present invention and are not intended to limit the scope of the present invention.

The present invention is a dual function sound attenuating and enhancing headpiece. The present invention is shown in FIGS. 1-6 and comprises a first acoustic assembly 1, a second acoustic assembly 2, a headband 14, and a wireless control unit 17.

Figure 1:
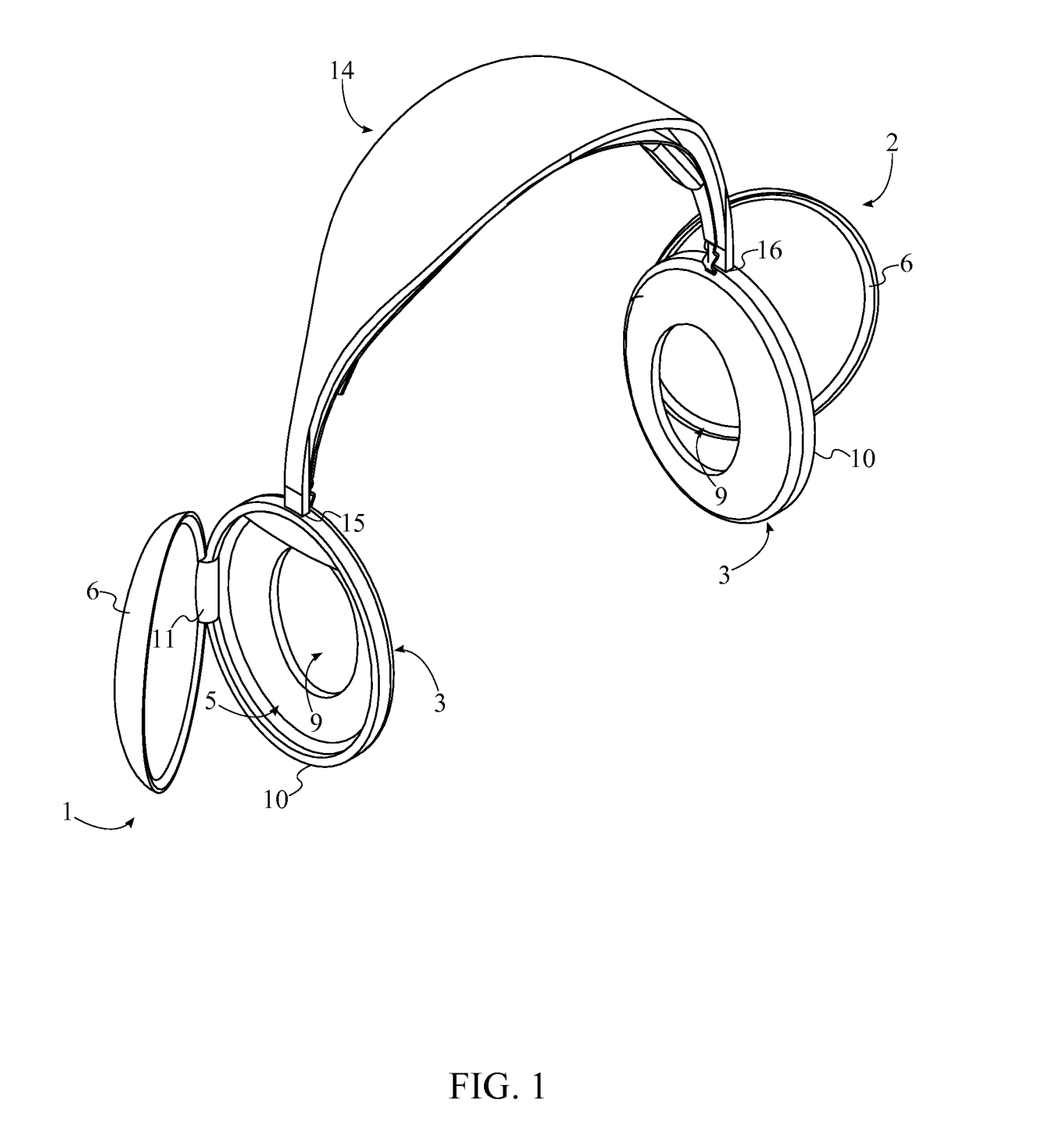
FIG. 1 is a perspective view of the present invention.

The first acoustic assembly 1 and the second acoustic assembly 2 are functionally identical and are able to block or enhance incoming sounds. The headband 14 connects the first acoustic assembly 1 and the second acoustic assembly 2 and additionally provides support for the present invention when worn on the user's head. As shown in FIG. 1, the first acoustic assembly 1 is connected to a first end 15 of the headband 14 while the second acoustic assembly 2 is connected to a second end 16 of the headband 14, opposite to the first acoustic assembly 1. As such, the first acoustic assembly 1 and the second acoustic assembly 2 may be positioned adjacent to the user's right ear and left ear, respectively.

Again with reference to FIGS. 1-6, the first acoustic assembly 1 and the second acoustic assembly 2 each comprise an earpiece 3, at least one acoustic-enhancing and attenuating cover 6, an ear opening 9, a lip 10, and at least one servomotor 11. The earpiece 3 is the component that is worn on the user's ear when the present invention is in use and comprises an open end 5. The open end 5 is the end of the earpiece 3 through which sound enters and may be closed by the at least one acoustic-enhancing and attenuating cover 6 in order to completely block sound. The at least one acoustic-enhancing and attenuating cover 6 is able to completely block sound when closed over the open end 5. The ear opening 9 allows the earpiece 3 to be secured to the user's ear. The ear opening 9 may simply be a flexible and stretchable hole through which the user's ear may be inserted or alternatively, the ear opening 9 may be an elongated channel that is inserted into the user's ear canal. The ear opening 9 may be large enough to simply surround the user's ear and allow the natural concavity of the user's ear to provide an acoustic effect as shown in FIG. 1. The natural concavity of the user's ear allows the user's ear to serve as a collector for incoming sound. The ear opening 9 traverses through the earpiece 3. The ear opening 9 is thus positioned adjacent to the user's ear and allows sound to be directed toward the user's ear when the at least one acoustic-enhancing and attenuating cover 6 is open.

Figure 2:
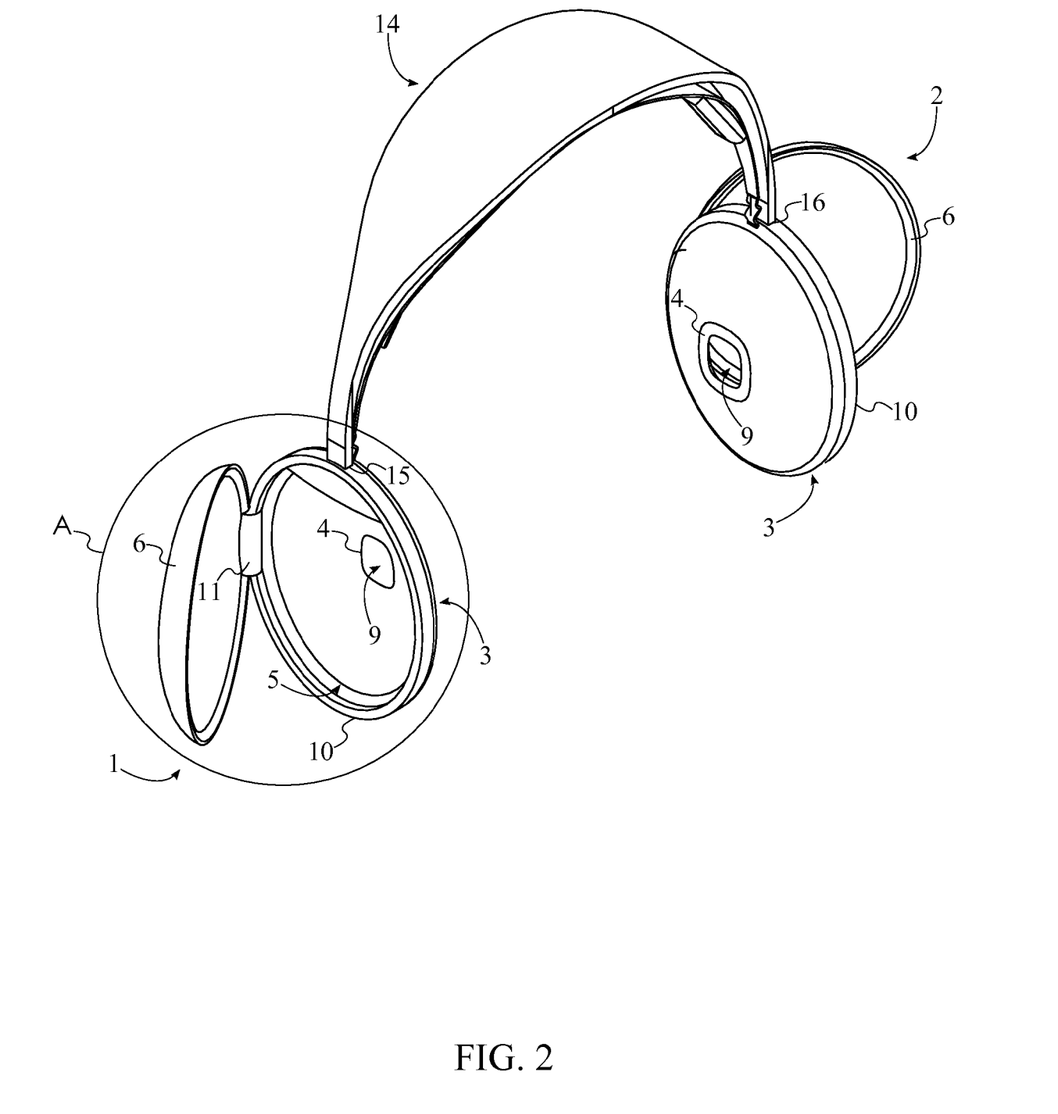
FIG. 2 is a perspective view of the present invention.
Figure 3:
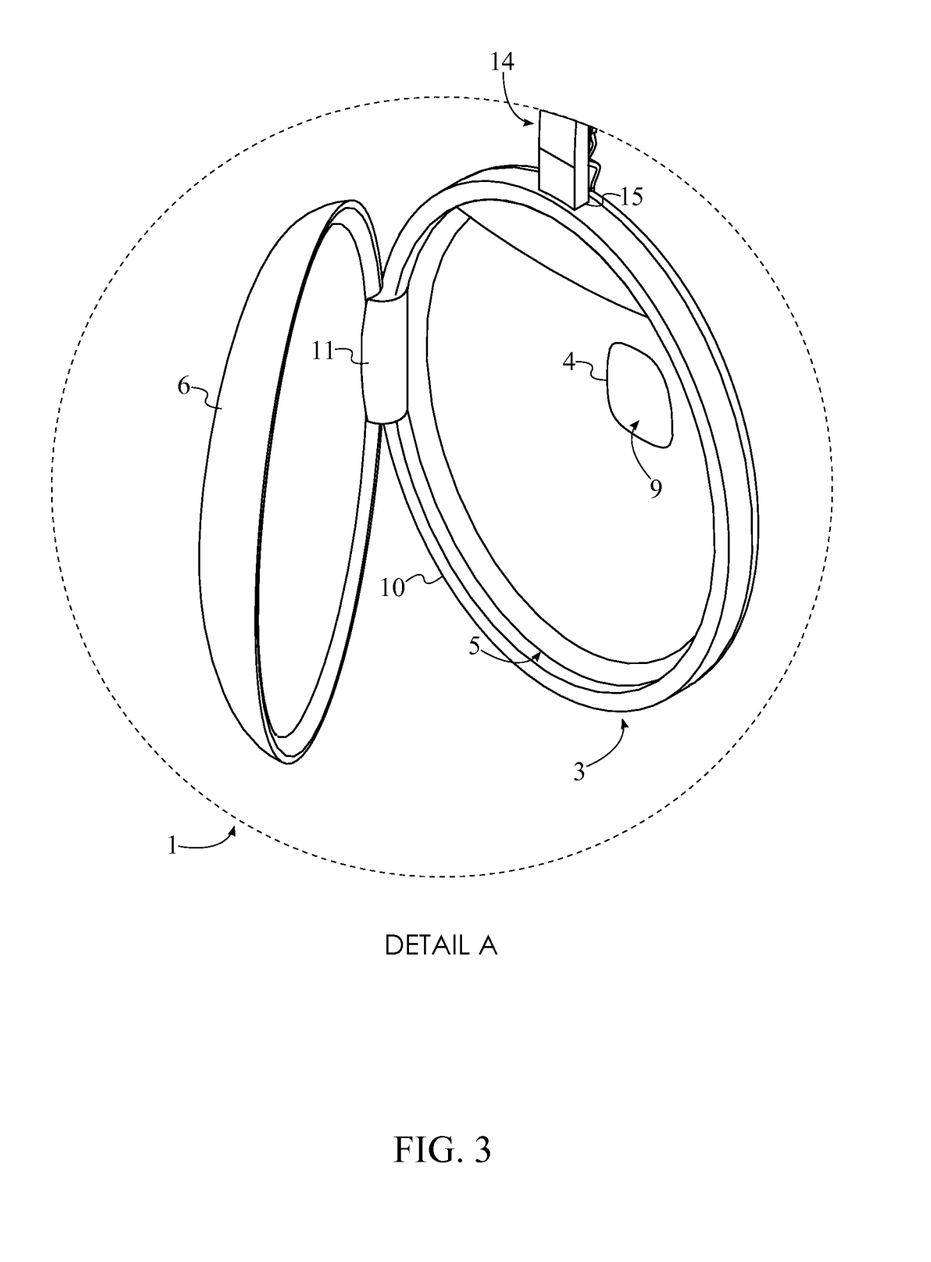
FIG. 3 is a detail view of the present invention taken from circle A of FIG. 1.

In the embodiment of the present invention shown in FIG. 2 and FIG. 3, the earpiece further comprises a concave end 4. The concave end 4 serves to produce an acoustic effect to any sound entering the earpiece 3. For example, the concave end 4 may produce an occlusion effect, causing the user to experience echo-like effects on sounds. The open end 5 is positioned in between the concave end 4 and the at least one acoustic-enhancing and attenuating cover 6, allowing the at least one acoustic-enhancing and attenuating cover 6 to be closed over the open end 5 and prevent sound from entering the concave end 4. The ear opening 9 additionally traverses through the concave end 4, positioning the ear opening 9 adjacent to the user's ear and allowing sound to be directed toward the user's ear.

Again with reference to FIGS. 1-6, the lip 10 provides a surface upon which the at least one acoustic-enhancing and attenuating cover 6 is able to rest when the at least one acoustic-enhancing and attenuating cover 6 is closed upon the open end 5. The lip 10 is circumferentially integrated about the open end 5 forming a surface around the open end 5 for the at least one acoustic-enhancing and attenuating cover 6.

Figure 4:
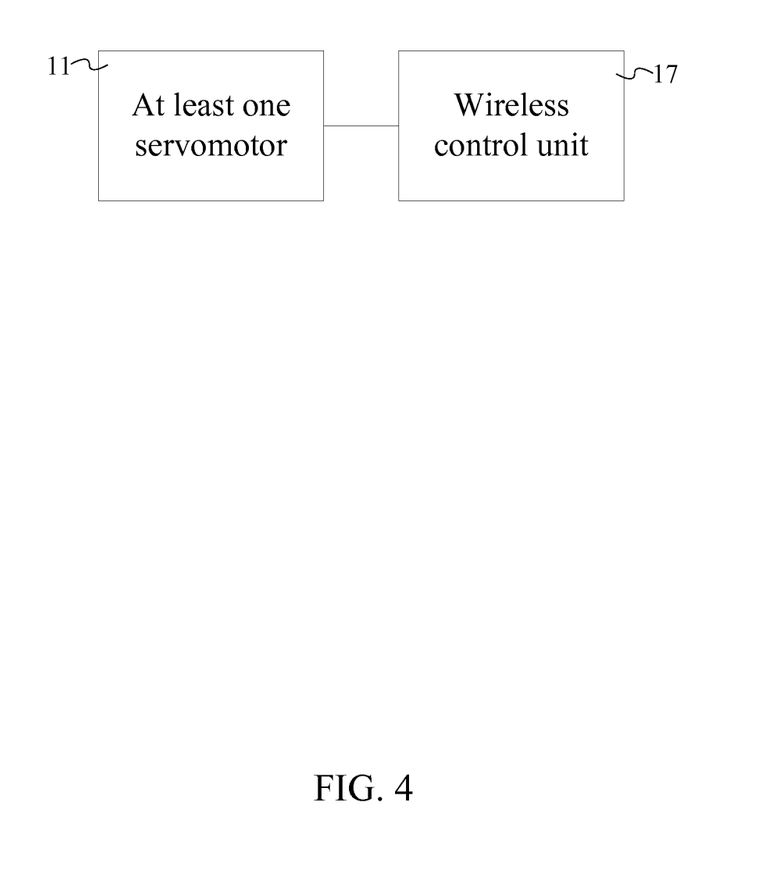
FIG. 4 is a diagram depicting the connection between the at least one servomotor and the wireless control unit.

The at least one servomotor 11 allows the at least one acoustic-enhancing and attenuating cover 6 to open or close over the open end 5. The at least one acoustic-enhancing and attenuating cover 6 is pivotally connected to the lip 10 by the at least one servomotor 11. The at least one acoustic-enhancing and attenuating cover 6 may thus be opened and closed to a precise degree as desired by the user. The at least one acoustic-enhancing and attenuating cover 6 is controlled via the wireless control unit 17. The wireless control unit 17 enables the user to wirelessly control the behavior of the at least one acoustic-enhancing and attenuating cover 6. The wireless control unit 17 is electronically connected to the at least one servomotor 11 as shown in FIG. 4. The wireless control unit 17 is thus able to adjust the at least one acoustic-enhancing and attenuating cover 6 through the at least one servomotor 11 as shown in FIGS. 1-3 based on wireless commands.

Figure 5:
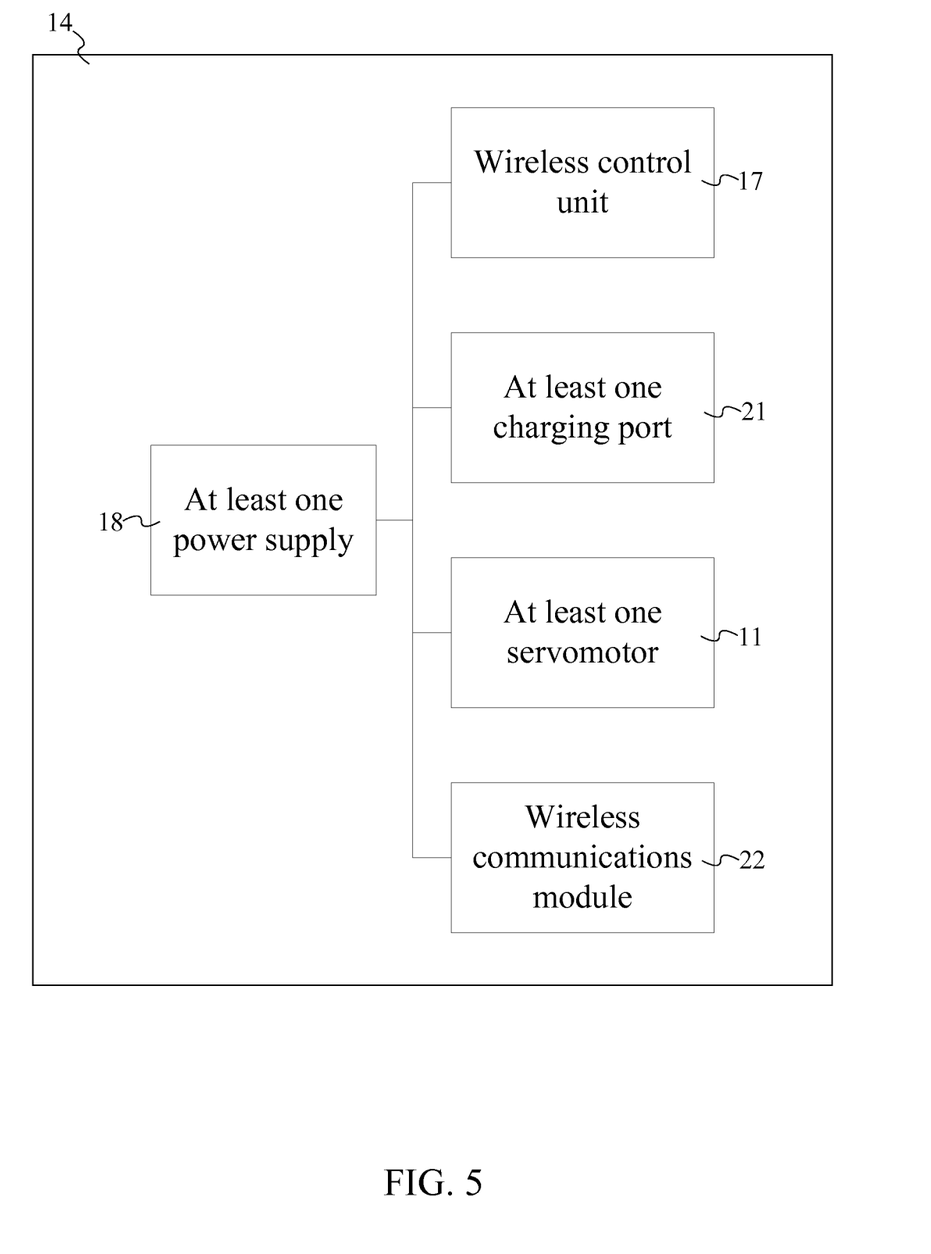
FIG. 5 is a diagram depicting the connection between the at least one power supply and the wireless control unit, the at least one charging port, and the at least one servomotor.
Figure 6:
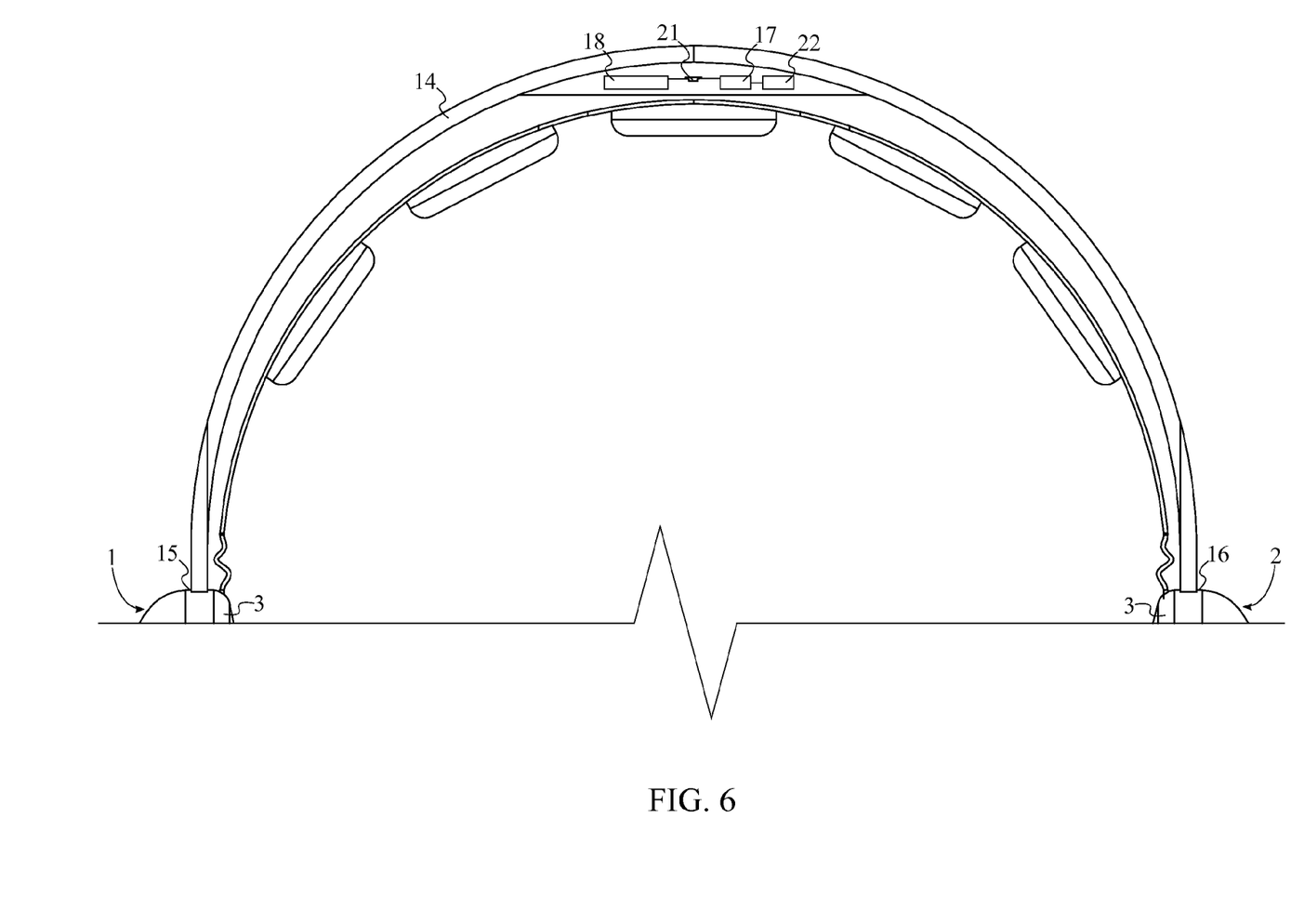
FIG. 6 is a rear view of an embodiment of the present invention, wherein the at least one power supply is enclosed within the headband.
Figure 7:
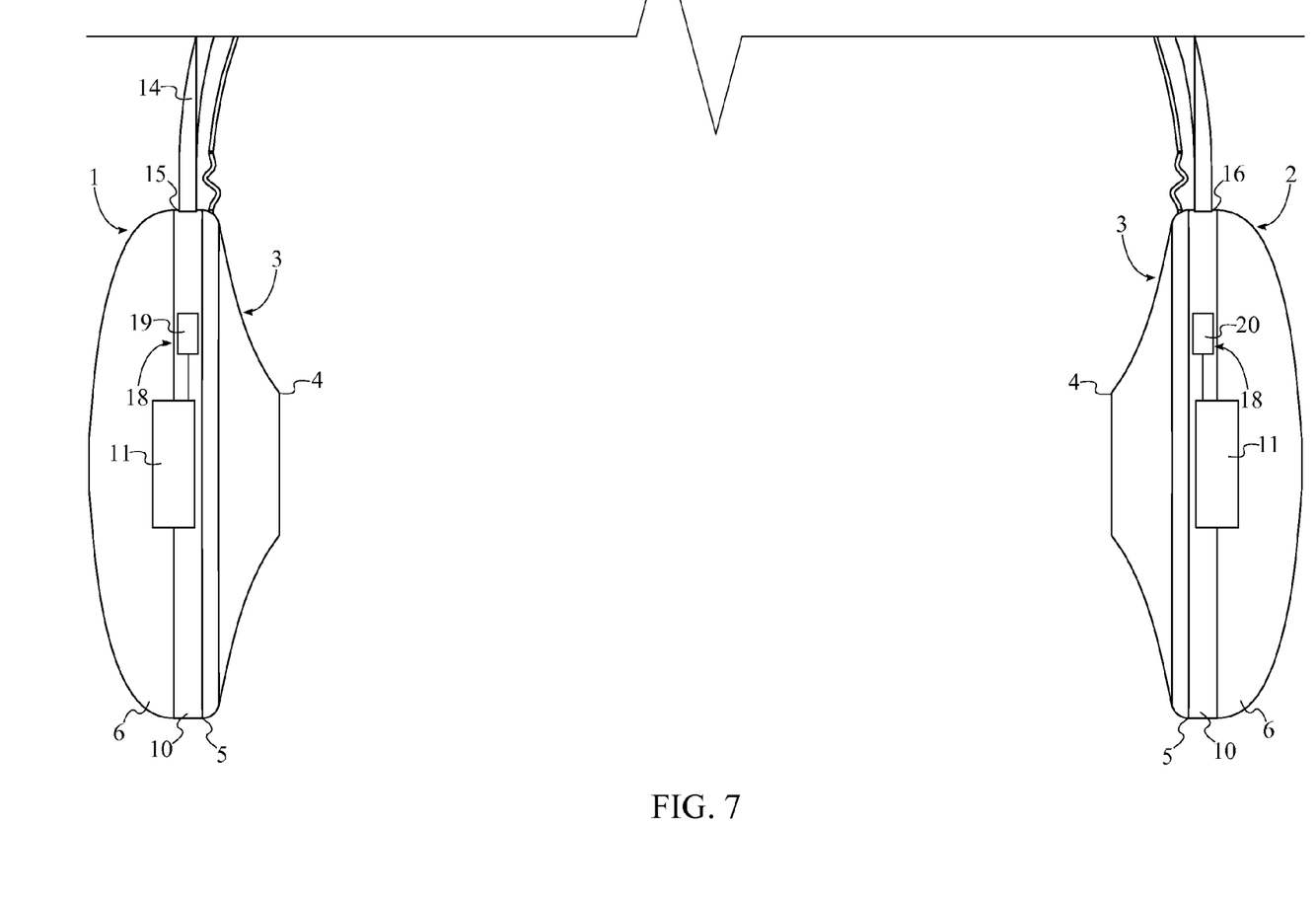
FIG. 7 is a rear view of the present invention depicting the location of the first power supply and the second power supply.

As shown in FIG. 5 and FIG. 6, the present invention further comprises at least one power supply 18 and at least one charging port 21. The at least one power supply 18 provides electrical power to the electronic components of the present invention. As such, the at least one power supply 18 is electrically connected to the at least one charging port 21, the at least one servomotor 11, and the wireless control unit 17. This allows the at least one power supply 18 to provide electrical power to the at least one servomotor 11 and the wireless control unit 17. Additionally, the at least one power supply 18 may be charged via the at least one charging port 21. In the embodiment of the present invention shown in FIG. 5 and FIG. 6, the at least one power supply 18 is enclosed within the headband 14. The at least one power supply 18 may be rechargeable or replaceable and may be positioned within a dedicated compartment with cover. The at least one power supply 18 is thus positioned in between the first acoustic assembly 1 and the second acoustic assembly 2 and is able to provide electrical power to both. The at least one charging port 21 traverses into the headband 14, allowing the user to easily charge the at least one power supply 18. In the embodiment of the present invention shown in FIG. 7, the at least one power supply 18 comprises a first power supply 19 and a second power supply 20. The first power supply 19 and the second power supply 20 provide power to the first acoustic assembly 1 and the second acoustic assembly 2, respectively. As such, the first acoustic assembly 1 and the second acoustic assembly 2 are each provided with electrical power from a dedicated power source. The first power supply 19 is enclosed within the earpiece 3 of the first acoustic assembly 1 and the second power supply 20 is enclosed within the earpiece 3 of the second acoustic assembly 2, allowing the first power supply 19 to provide electrical power to the first acoustic assembly 1 and the second power supply 20 to provide electrical power to the second acoustic assembly 2. Alternatively, the at least one power supply 18 may be positioned independent of the first acoustic assembly 1, the second acoustic assembly 2, and the headband 14. For example, the at least one power supply 18 may be worn somewhere on the user's body and connected to the remaining electronic components of the present invention via a wire.

Again with reference to FIG. 6, the present invention further comprises a wireless communications module 22. The wireless communications module 22 enables wireless communication between the present invention and a user electronic device such as a remote control or smartphone. The wireless communications module 22 is enclosed within the headband 14 and is able to receive commands from the user electronic device. The wireless communications module 22 is electronically connected to the wireless control unit 17 and wireless commands received from the user electronic device are transmitted to the wireless control unit 17. A mobile application may be utilized on the user electronic device in order to control the present invention.

Figure 8:
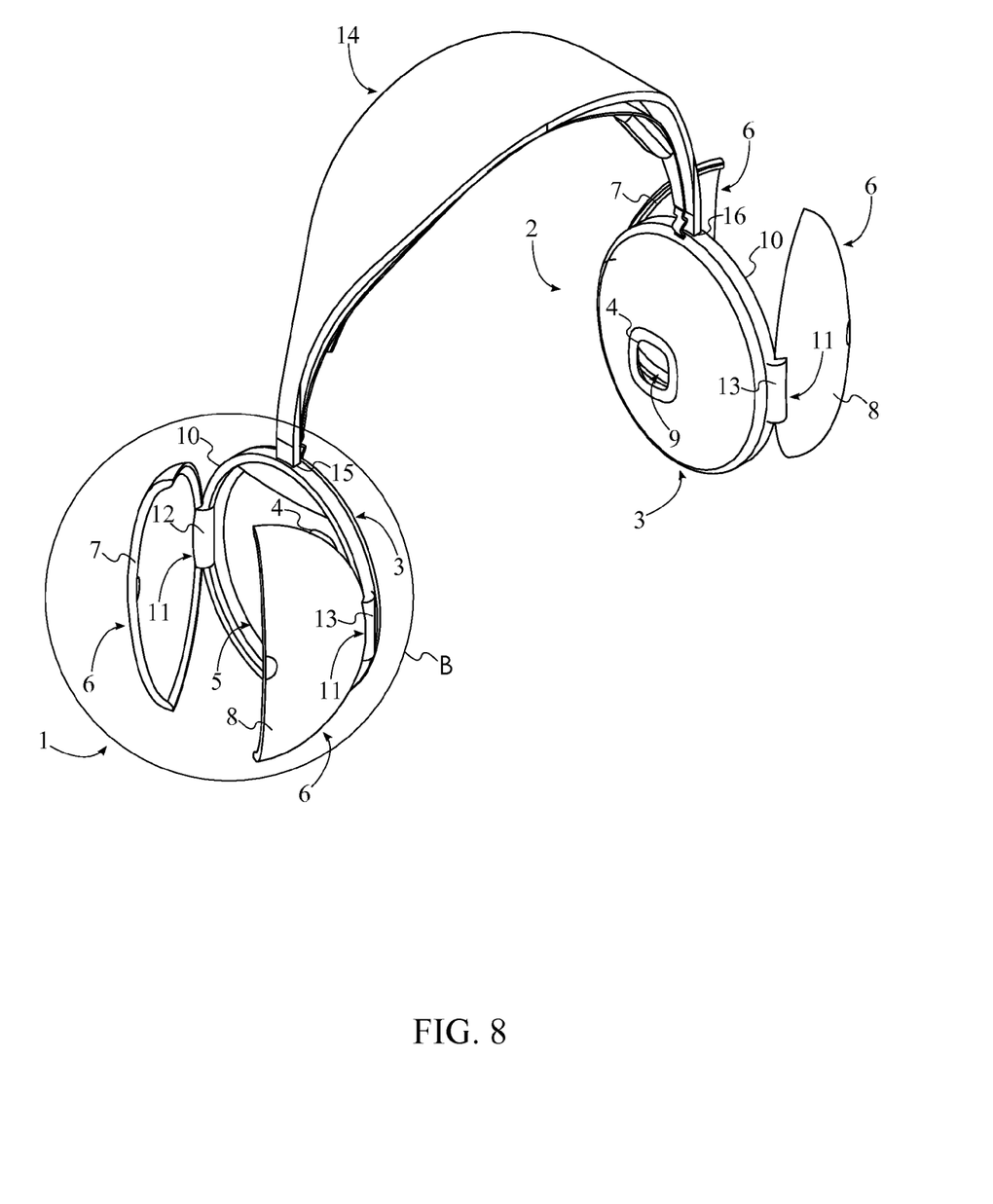
FIG. 8 is a perspective view of an embodiment of the present invention with the first half cover and the second half cover.
Figure 9:
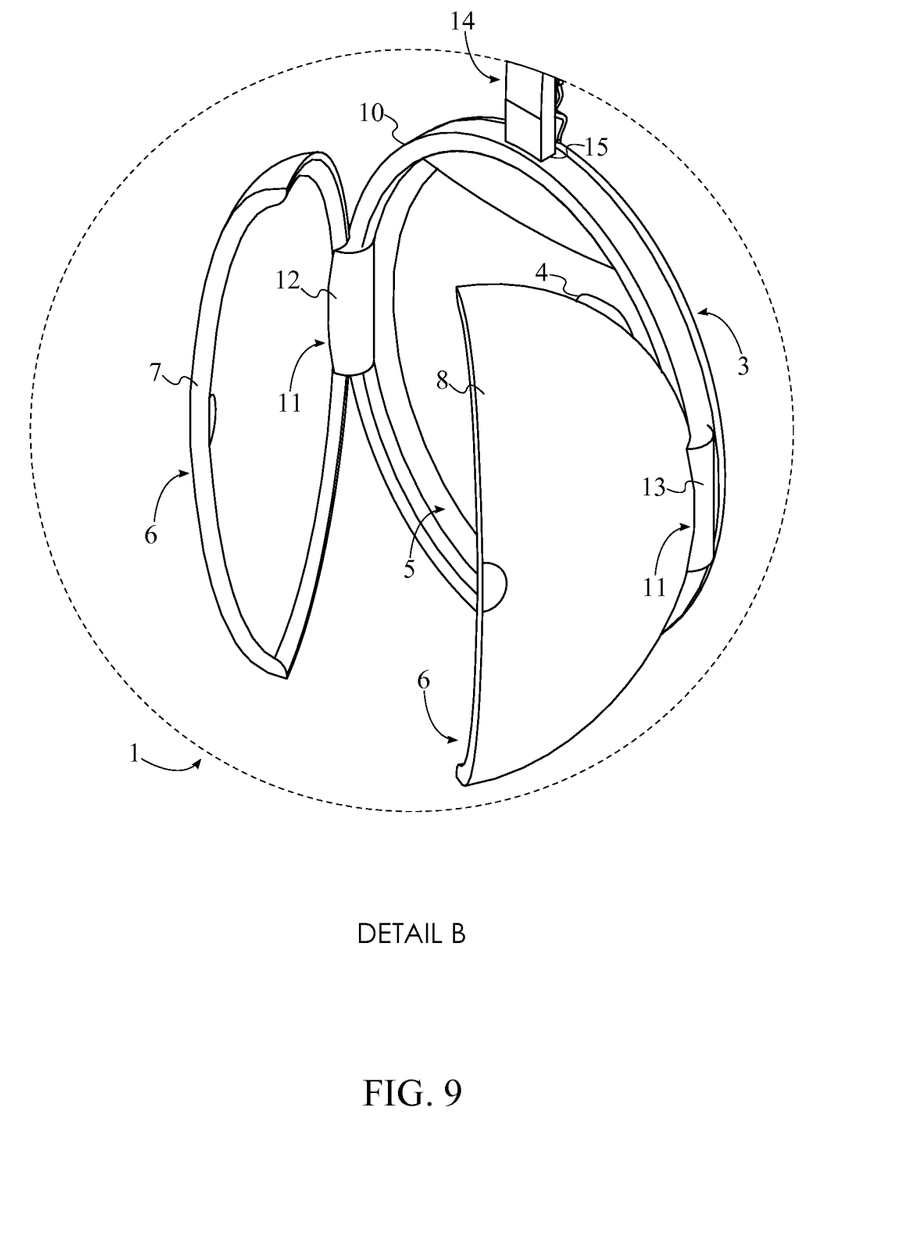
FIG. 9 is a detail view of the present invention taken from circle B of FIG. 7.

The at least one acoustic-enhancing and attenuating cover 6 comprises a first half cover 7 and a second half cover 8 in the embodiment of the present invention shown in FIG. 8 and FIG. 9. The first half cover 7 and the second half cover 8 provide bidirectional influence on sound entering the first acoustic assembly 1 and the second acoustic assembly 2. As such, the user is able to adjust the first acoustic assembly 1 and the second acoustic assembly 2 in order to produce an acoustic effect on sound that originates from in front of and behind the user. The at least one servomotor 11 comprises a first servomotor 12 and a second servomotor 13. The first servomotor 12 and the second servomotor 13 allow for adjustment of the first half cover 7 and the second half cover 8, respectively. The first half cover 7 is pivotally connected to the lip 10 by the first servomotor 12 while the second half cover 8 is pivotally connected to the lip 10 by the second servomotor 13, opposite to the first half cover 7. The first servomotor 12 may thus be used to open or close the first half cover 7 to a precise degree while the second servomotor 13 provides the same functionality to the second half cover 8.

Figure 12:
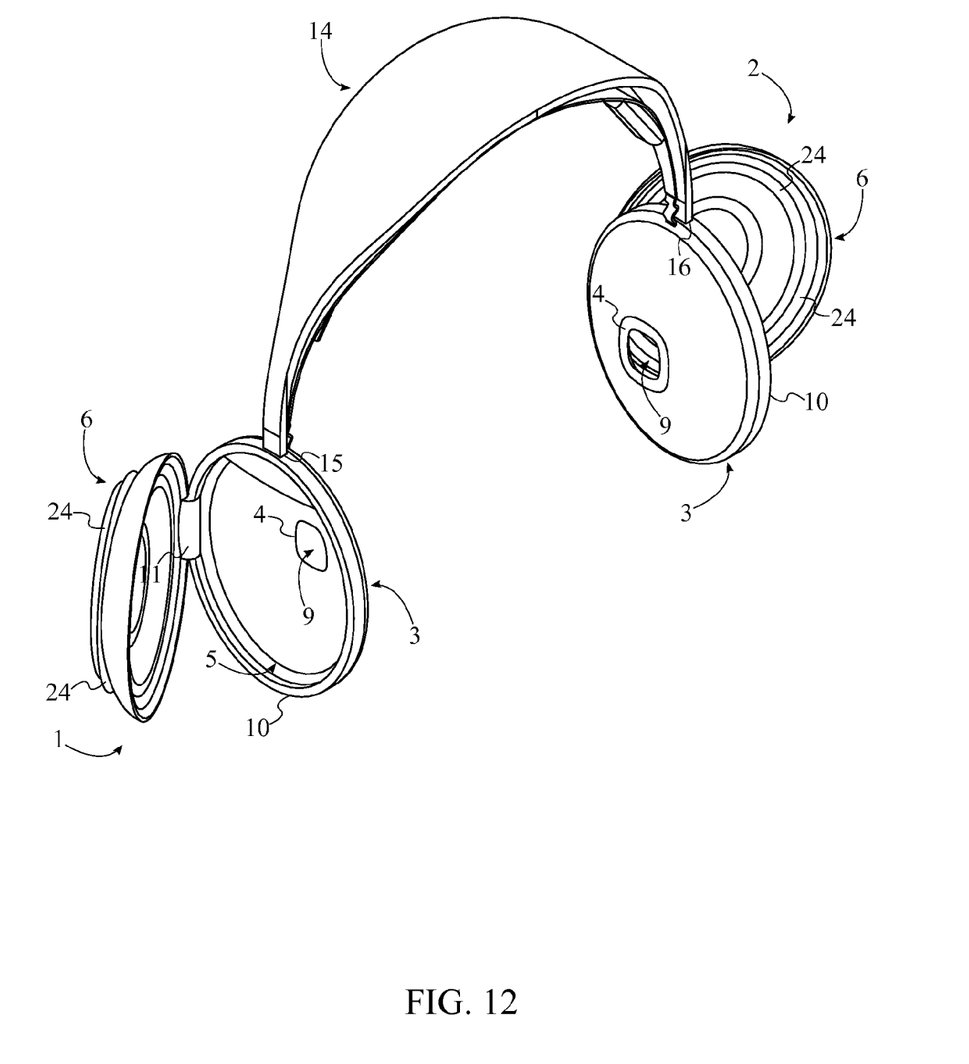
FIG. 12 is a perspective view of an embodiment of the present invention with the plurality of acoustic-altering layers.

In the embodiment of the present invention shown in FIG. 12, the at least one acoustic-enhancing and attenuating cover 6 comprises a plurality of acoustic-altering layers 24. The plurality of acoustic-altering layers 24 is able to dampen or absorb sound depending on the external or internal positioning of the plurality of acoustic-altering layers 24 on the at least one acoustic-enhancing and attenuating cover 6. The plurality of acoustic-altering layers 24 is layered upon each other, allowing the plurality of acoustic-altering layers 24 to exert an acoustic effect on incoming sound. The plurality of acoustic-altering layers 24 may be composed of various materials including, but not limited to, wood, polymers, and acoustic foams.

Figure 10:
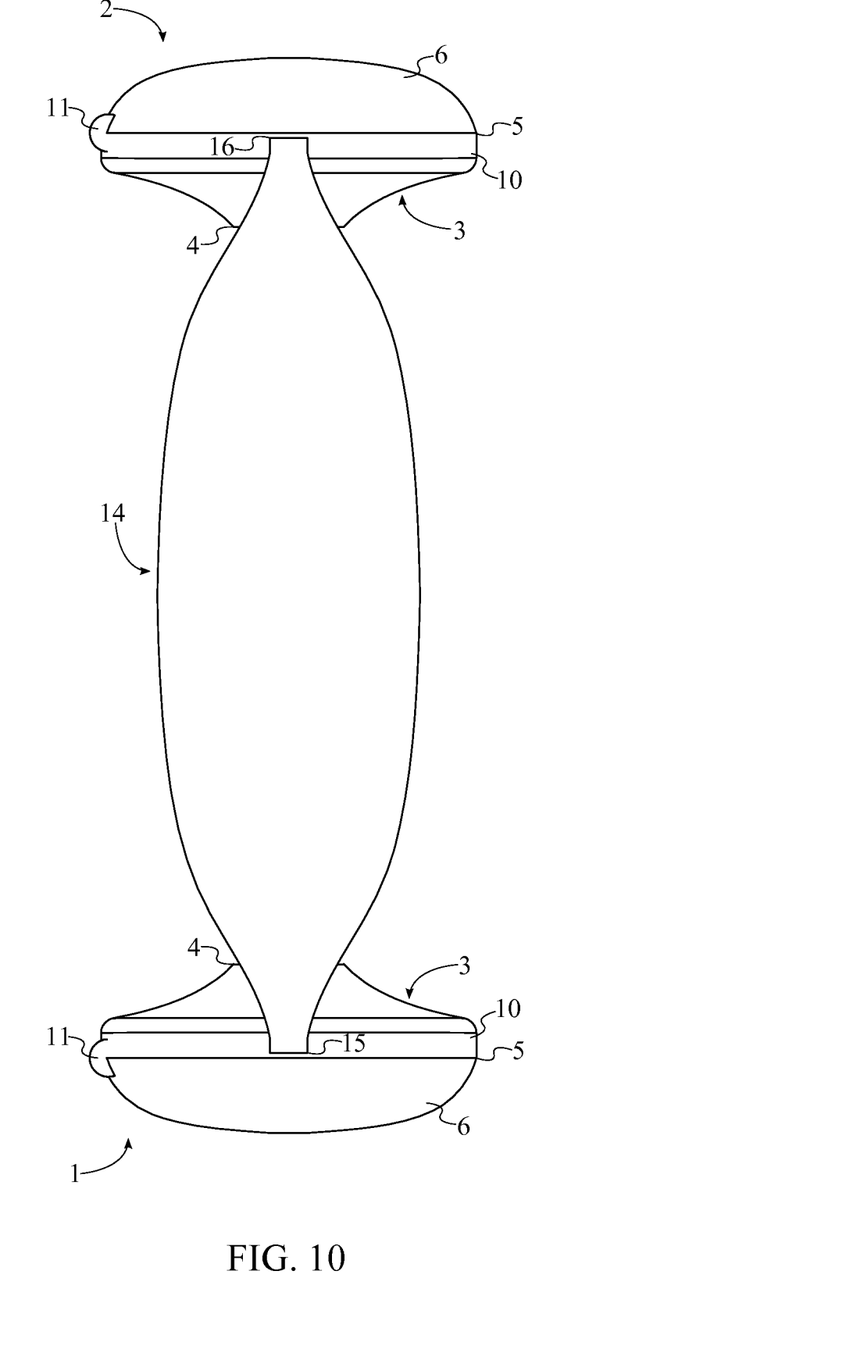
FIG. 10 is a top view of the present invention in an audio-blocking configuration.

In the configuration of the present invention shown in FIG. 10, the at least one acoustic-enhancing and attenuating cover 6 is in an audio-blocking configuration. The audio-blocking configuration is used when the user wishes to block all sound from entering his or her ears. As such, the at least one acoustic-enhancing and attenuating cover 6 is coincident with the lip 10, adjacent to the open end 5. This forms a seal between the at least one acoustic-enhancing and attenuating cover 6 and the open end 5, preventing sound from entering the open end 5.

Figure 11:
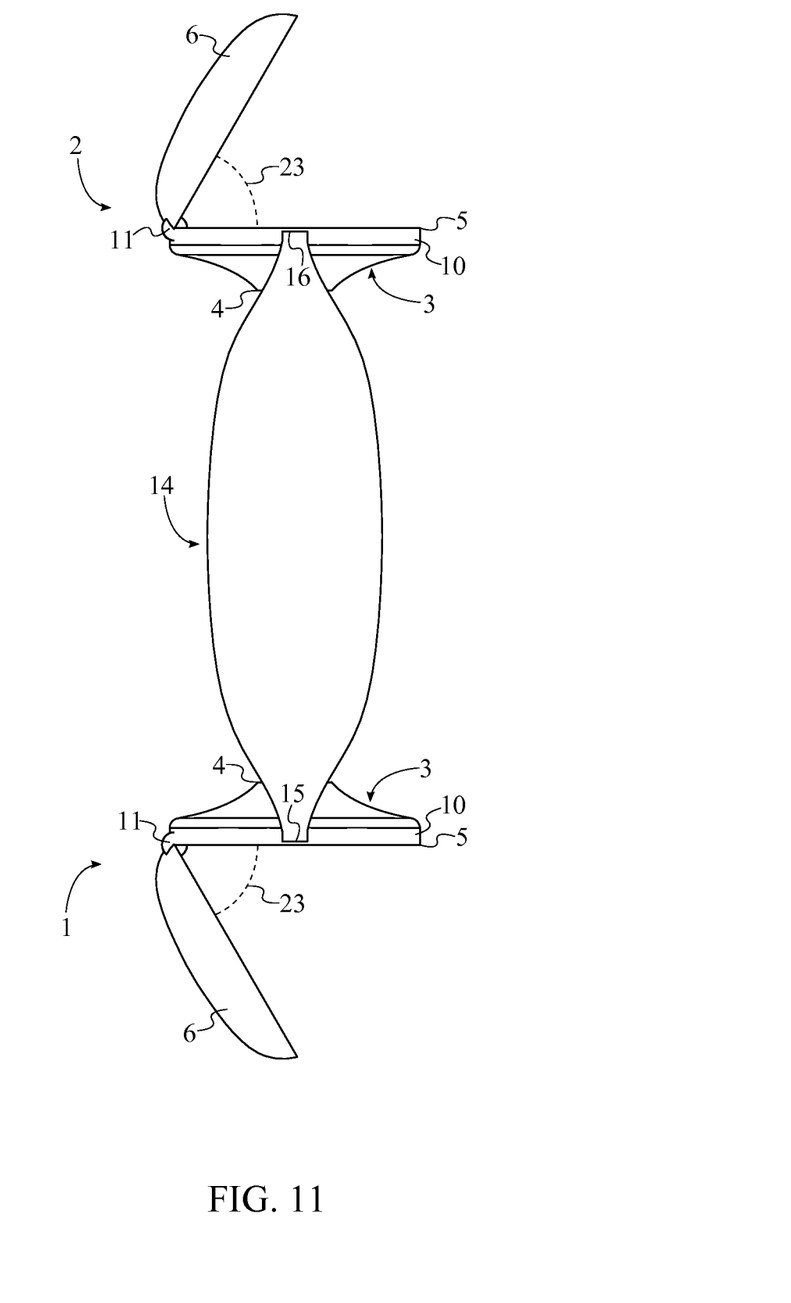
FIG. 11 is a top view of the present invention in an audio-enhancing configuration.

In the configuration of the present invention shown in FIG. 11, the at least one acoustic-enhancing and attenuating cover 6 is in an audio-enhancing configuration. The audio-enhancing configuration is used when the user wishes to produce an acoustic effect on sound via the at least one acoustic-enhancing and attenuating cover 6. The at least one acoustic-enhancing and attenuating cover 6 is angularly offset from the lip 10 by an enhancing angle 23. The enhancing angle 23 is an indicator of the degree to which the at least one acoustic-enhancing and attenuating cover 6 is opened to produce an acoustic effect.

Although the present invention has been explained in relation to its preferred embodiment, it is understood that many other possible modifications and variations can be made without departing from the spirit and scope of the present invention as hereinafter claimed.

What is claimed is:

1. A dual function sound attenuating and enhancing headpiece comprises:
    a first acoustic assembly;
    a second acoustic assembly;
    a headband;
    a wireless control unit;
    the first acoustic assembly and the second acoustic assembly each comprise an earpiece, at least one acoustic-enhancing and attenuating cover, an ear opening, a lip, and at least one servomotor;
    the earpiece comprises an open end;
    the first acoustic assembly being connected to a first end of the headband;
    the second acoustic assembly being connected to a second end of the headband, opposite to the first acoustic assembly;
    the lip being circumferentially integrated about the open end;
    the ear opening traversing through the earpiece;
    the at least one acoustic-enhancing and attenuating cover being pivotally connected to the lip by the at least one servomotor; and
    the wireless control unit being electronically connected to the at least one servomotor.

2. The dual function sound attenuating and enhancing headpiece as claimed in claim 1 further comprises:
    the earpiece further comprises a concave end;
    the open end being positioned in between the concave end and the at least one acoustic-enhancing and attenuating cover; and
    the ear opening traversing through the concave end.

3. The dual function sound attenuating and enhancing headpiece as claimed in claim 1 further comprises:
    at least one power supply;
    at least one charging port; and
    the at least one power supply being electrically connected to the at least one charging port, the at least one servomotor, and the wireless control unit.

4. The dual function sound attenuating and enhancing headpiece as claimed in claim 3 further comprises:
    the at least one power supply being enclosed within the headband; and
    the at least one charging port traversing into the headband.

5. The dual function sound attenuating and enhancing headpiece as claimed in claim 3 further comprises:
    the at least one power supply comprises a first power supply and a second power supply;
    the first power supply being enclosed within the earpiece of the first acoustic assembly; and
    the second power supply being enclosed within the earpiece of the second acoustic assembly.

6. The dual function sound attenuating and enhancing headpiece as claimed in claim 1 further comprises:
    a wireless communications module;
    the wireless communications module being enclosed within the headband; and
    the wireless communications module being electronically connected to the wireless control unit.

7. The dual function sound attenuating and enhancing headpiece as claimed in claim 1 further comprises:
    the at least one acoustic-enhancing and attenuating cover comprises a first half cover and a second half cover;
    the at least one servomotor comprises a first servomotor and a second servomotor;
    the first half cover being pivotally connected to the lip by the first servomotor; and
    the second half cover being pivotally connected to the lip by the second servomotor, opposite to the first half cover.

8. The dual function sound attenuating and enhancing headpiece as claimed in claim 1 further comprises:
    the at least one acoustic-enhancing and attenuating cover comprises a plurality of acoustic-altering layers; and
    the plurality of acoustic-altering layers being layered upon each other.

9. The dual function sound attenuating and enhancing headpiece as claimed in claim 1 further comprises:
    the at least one acoustic-enhancing and attenuating cover being coincident with the lip, adjacent to the open end; and
    wherein the at least one acoustic-enhancing and attenuating cover is in an audio-blocking configuration.

10. The dual function sound attenuating and enhancing headpiece as claimed in claim 1 further comprises:
    the at least one acoustic-enhancing and attenuating cover being angularly offset from the lip by an enhancing angle; and
    wherein the at least one acoustic-enhancing and attenuating cover is in an audio-enhancing configuration.

11. A dual function sound attenuating and enhancing headpiece comprises:
a first acoustic assembly;
a second acoustic assembly;
a headband;
a wireless control unit;
the first acoustic assembly and the second acoustic assembly each comprise an earpiece, at least one acoustic-enhancing and attenuating cover, an ear opening, a lip, and at least one servomotor;
the earpiece comprises an open end and a concave end;
the first acoustic assembly being connected to a first end of the headband;
the second acoustic assembly being connected to a second end of the headband, opposite to the first acoustic assembly;
the lip being circumferentially integrated about the open end;
the ear opening traversing through the earpiece;
the at least one acoustic-enhancing and attenuating cover being pivotally connected to the lip by the at least one servomotor;
the wireless control unit being electronically connected to the at least one servomotor;
the open end being positioned in between the concave end and the at least one acoustic-enhancing and attenuating cover; and
the ear opening traversing through the concave end.

12. The dual function sound attenuating and enhancing headpiece as claimed in claim 1 further comprises:
at least one power supply;
at least one charging port; and
the at least one power supply being electrically connected to the at least one charging port, the at least one servomotor, and the wireless control unit.

13. The dual function sound attenuating and enhancing headpiece as claimed in claim 12 further comprises:
the at least one power supply being enclosed within the headband; and
the at least one charging port traversing into the headband.

14. The dual function sound attenuating and enhancing headpiece as claimed in claim 12 further comprises:
the at least one power supply comprises a first power supply and a second power supply;
the first power supply being enclosed within the earpiece of the first acoustic assembly; and
the second power supply being enclosed within the earpiece of the second acoustic assembly.

15. The dual function sound attenuating and enhancing headpiece as claimed in claim 1 further comprises:
a wireless communications module;
the wireless communications module being enclosed within the headband; and
the wireless communications module being electronically connected to the wireless control unit.

16. The dual function sound attenuating and enhancing headpiece as claimed in claim 1 further comprises:
the at least one acoustic-enhancing and attenuating cover comprises a first half cover and a second half cover;
the at least one servomotor comprises a first servomotor and a second servomotor;
the first half cover being pivotally connected to the lip by the first servomotor; and
the second half cover being pivotally connected to the lip by the second servomotor, opposite to the first half cover.

17. The dual function sound attenuating and enhancing headpiece as claimed in claim 1 further comprises:
the at least one acoustic-enhancing and attenuating cover comprises a plurality of acoustic-altering layers; and
the plurality of acoustic-altering layers being layered upon each other.

18. The dual function sound attenuating and enhancing headpiece as claimed in claim 1 further comprises:
the at least one acoustic-enhancing and attenuating cover being coincident with the lip, adjacent to the open end; and
wherein the at least one acoustic-enhancing and attenuating cover is in an audio-blocking configuration.

19. The dual function sound attenuating and enhancing headpiece as claimed in claim 1 further comprises:
the at least one acoustic-enhancing and attenuating cover being angularly offset from the lip by an enhancing angle; and
wherein the at least one acoustic-enhancing and attenuating cover is in an audio-enhancing configuration.

* * * * *